(12) United States Patent
Scheiner et al.

(10) Patent No.: US 7,572,226 B2
(45) Date of Patent: Aug. 11, 2009

(54) SYSTEM AND METHOD FOR MONITORING AUTONOMIC BALANCE AND PHYSICAL ACTIVITY

(75) Inventors: Avram Scheiner, Vadnais Heights, MN (US); Donald Hopper, Maple Grove, MN (US); Gerrard M. Carlson, Champlin, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 755 days.

(21) Appl. No.: 10/695,430

(22) Filed: Oct. 28, 2003

(65) Prior Publication Data

US 2005/0090719 A1 Apr. 28, 2005

(51) Int. Cl.
*A61B 5/00* (2006.01)
(52) U.S. Cl. .......................... 600/485; 600/500; 600/508
(58) Field of Classification Search .................. None
See application file for complete search history.

(56) References Cited

U.S. PATENT DOCUMENTS

| | | | |
|---|---|---|---|
| 3,618,593 A | 11/1971 | Nachev et al. |
| 4,114,627 A | 9/1978 | Lewyn et al. |
| 4,404,972 A | 9/1983 | Gordon et al. |
| 4,777,960 A | 10/1988 | Berger et al. |
| 4,791,931 A | 12/1988 | Slate |
| 4,830,006 A | 5/1989 | Haluska et al. |
| 4,872,459 A | 10/1989 | Pless et al. |
| 4,880,005 A | 11/1989 | Pless et al. |
| 4,945,909 A | 8/1990 | Fearnot et al. |
| 5,014,698 A | 5/1991 | Cohen |
| 5,025,786 A | 6/1991 | Siegel |
| 5,063,927 A | 11/1991 | Webb et al. |
| 5,111,815 A | 5/1992 | Mower |
| 5,183,040 A | 2/1993 | Nappholz et al. |

(Continued)

FOREIGN PATENT DOCUMENTS

EP 0555988 A2 8/1993

(Continued)

OTHER PUBLICATIONS

"Heart Rate Variability: Standards of Measurement, Physiological Interpretation, and Clinical Use", *European Heart Journal*, 17, Prepared by the Task Force of The European Society of Cardiology and The North American Society of Pacing and Electrophysiology; published by the American Heart Association, Inc.; European Society of Cardiology,(1996),pp. 354-381.

(Continued)

*Primary Examiner*—Robert L Nasser
(74) *Attorney, Agent, or Firm*—Schwegman, Lundberg & Woessner, P.A.

(57) ABSTRACT

An implantable device monitors the balance between sympathetic tone and parasympathetic tone as a function of an activity level. Cardio-neurological healthy users exhibit a generally sympathetic tone in conjunction with heavy activity level and a generally parasympathetic tone in conjunction with periods of low activity level. Deviations from expected results are associated with a health problem. Measured conditions are stored and available for subsequent reporting to a remote programmer. Therapy delivered by an implantable device is determined as a function of the relationship between autonomic balance and activity level.

20 Claims, 3 Drawing Sheets

U.S. PATENT DOCUMENTS

| | | |
|---|---|---|
| 5,190,035 A | 3/1993 | Salo et al. |
| 5,197,467 A | 3/1993 | Steinhaus et al. |
| 5,199,428 A | 4/1993 | Obel et al. |
| 5,201,808 A | 4/1993 | Steinhaus et al. |
| 5,203,326 A | 4/1993 | Collins |
| 5,222,493 A | 6/1993 | Sholder |
| 5,243,980 A | 9/1993 | Mehra |
| 5,269,301 A | 12/1993 | Cohen |
| 5,273,034 A | 12/1993 | Nilsson |
| 5,300,093 A | 4/1994 | Koestner et al. |
| 5,303,702 A | 4/1994 | Bonnet et al. |
| 5,318,592 A | 6/1994 | Schaldach |
| 5,318,597 A | 6/1994 | Hauck et al. |
| 5,324,310 A | 6/1994 | Greeninger et al. |
| 5,330,507 A | 7/1994 | Schwartz |
| 5,331,966 A | 7/1994 | Bennett et al. |
| 5,341,811 A | 8/1994 | Cano |
| 5,354,317 A | 10/1994 | Alt |
| 5,356,425 A | 10/1994 | Bardy et al. |
| 5,360,436 A | 11/1994 | Alt et al. |
| 5,391,190 A | 2/1995 | Pederson et al. |
| 5,411,531 A | 5/1995 | Hill et al. |
| 5,423,870 A | 6/1995 | Olive et al. |
| 5,431,685 A | 7/1995 | Alt |
| 5,431,687 A | 7/1995 | Kroll |
| 5,437,285 A | 8/1995 | Verrier et al. |
| 5,441,524 A | 8/1995 | Rueter et al. |
| 5,443,485 A | 8/1995 | Housworth et al. |
| 5,466,245 A | 11/1995 | Spinelli et al. |
| 5,480,412 A | 1/1996 | Mouchawar et al. |
| 5,487,752 A | 1/1996 | Salo et al. |
| 5,507,784 A | 4/1996 | Hill et al. |
| 5,507,785 A | 4/1996 | Deno |
| 5,522,854 A | 6/1996 | Ideker et al. |
| 5,531,772 A | 7/1996 | Prutchi |
| 5,535,752 A | 7/1996 | Halperin et al. |
| 5,560,370 A | 10/1996 | Verrier et al. |
| 5,562,711 A | 10/1996 | Yerich et al. |
| 5,562,712 A | 10/1996 | Steinhaus et al. |
| 5,571,144 A | 11/1996 | Schroeppel |
| 5,578,061 A | 11/1996 | Stroetmann et al. |
| 5,601,615 A | 2/1997 | Markowitz et al. |
| 5,603,331 A | 2/1997 | Heemels et al. |
| 5,626,622 A | 5/1997 | Cooper |
| 5,626,624 A | 5/1997 | Schaldach et al. |
| 5,645,570 A | 7/1997 | Corbucci |
| 5,658,318 A | 8/1997 | Stroetmann et al. |
| 5,682,901 A | 11/1997 | Kamen |
| 5,685,316 A | 11/1997 | Schookin et al. |
| 5,690,681 A | 11/1997 | Geddes et al. |
| 5,700,282 A | 12/1997 | Zabara |
| 5,700,283 A | 12/1997 | Salo |
| 5,718,720 A | 2/1998 | Prutchi et al. |
| 5,722,997 A | 3/1998 | Nedungadi et al. |
| 5,749,900 A | 5/1998 | Schroeppel et al. |
| 5,755,671 A | 5/1998 | Albrecht et al. |
| 5,766,225 A | 6/1998 | Kramm |
| 5,782,884 A | 7/1998 | Stotts et al. |
| 5,792,194 A | 8/1998 | Morra |
| 5,817,135 A | 10/1998 | Cooper et al. |
| 5,817,136 A | 10/1998 | Nappholz et al. |
| 5,824,020 A | 10/1998 | Cooper |
| 5,824,029 A | 10/1998 | Weijand et al. |
| 5,842,997 A | 12/1998 | Verrier et al. |
| 5,843,136 A | 12/1998 | Zhu et al. |
| 5,861,012 A | 1/1999 | Stroebel |
| 5,873,898 A | 2/1999 | Hemming et al. |
| 5,891,044 A | 4/1999 | Golosarsky et al. |
| 5,893,882 A | 4/1999 | Peterson et al. |
| 5,916,239 A | 6/1999 | Geddes et al. |
| 5,921,940 A | 7/1999 | Verrier et al. |
| 5,935,081 A | 8/1999 | Kadhiresan |
| 5,978,707 A | 11/1999 | Krig et al. |
| 5,978,710 A | 11/1999 | Prutchi et al. |
| 5,987,356 A | 11/1999 | DeGroot |
| 6,006,134 A | 12/1999 | Hill et al. |
| 6,021,351 A | 2/2000 | Kadhiresan et al. |
| 6,022,322 A | 2/2000 | Prutchi |
| 6,026,320 A | 2/2000 | Carlson et al. |
| 6,035,233 A | 3/2000 | Schroeppel et al. |
| 6,042,548 A | 3/2000 | Giuffre |
| 6,044,294 A | 3/2000 | Mortazavi et al. |
| 6,058,331 A | 5/2000 | King |
| 6,073,048 A | 6/2000 | Kieval et al. |
| 6,076,015 A | 6/2000 | Hartley et al. |
| 6,128,526 A | 10/2000 | Stadler et al. |
| 6,128,535 A | 10/2000 | Maarse |
| 6,134,470 A | 10/2000 | Hartlaub |
| 6,135,970 A | 10/2000 | Kadhiresan et al. |
| 6,144,878 A | 11/2000 | Schroeppel et al. |
| 6,151,524 A | 11/2000 | Krig et al. |
| 6,161,042 A | 12/2000 | Hartley et al. |
| 6,167,308 A | 12/2000 | DeGroot |
| 6,178,349 B1 | 1/2001 | Kieval |
| 6,181,966 B1 | 1/2001 | Nigam |
| 6,216,032 B1 | 4/2001 | Griffin et al. |
| 6,224,553 B1 | 5/2001 | Nevo |
| 6,238,422 B1 | 5/2001 | Oort |
| 6,240,314 B1 | 5/2001 | Plicchi et al. |
| 6,246,909 B1 | 6/2001 | Ekwall |
| 6,269,263 B1 | 7/2001 | Ohnishi et al. |
| 6,273,856 B1 | 8/2001 | Sun et al. |
| 6,292,693 B1 | 9/2001 | Darvish et al. |
| 6,292,695 B1 | 9/2001 | Webster, Jr. et al. |
| 6,301,499 B1 | 10/2001 | Carlson et al. |
| 6,317,632 B1 | 11/2001 | Krig et al. |
| 6,358,201 B1 | 3/2002 | Childre et al. |
| 6,370,424 B1 | 4/2002 | Prutchi |
| 6,371,922 B1 | 4/2002 | Baumann et al. |
| 6,390,986 B1 | 5/2002 | Curcie et al. |
| 6,421,557 B1 | 7/2002 | Meyer |
| 6,424,865 B1 | 7/2002 | Ding |
| 6,430,441 B1 | 8/2002 | Levine |
| 6,438,421 B1 | 8/2002 | Stahmann et al. |
| 6,449,507 B1 | 9/2002 | Hill et al. |
| 6,453,201 B1 | 9/2002 | Daum et al. |
| 6,456,880 B1 | 9/2002 | Park et al. |
| 6,459,929 B1 | 10/2002 | Hopper et al. |
| 6,463,326 B1 | 10/2002 | Hartley et al. |
| 6,473,644 B1 | 10/2002 | Terry, Jr. et al. |
| 6,473,647 B1 | 10/2002 | Bradley |
| 6,480,733 B1 | 11/2002 | Turcott |
| 6,480,742 B2 | 11/2002 | Stahmann et al. |
| 6,487,450 B1 | 11/2002 | Chen |
| 6,493,585 B2 | 12/2002 | Plicchi et al. |
| 6,511,500 B1 | 1/2003 | Rahme |
| 6,522,914 B1 | 2/2003 | Huvelle |
| 6,522,926 B1 | 2/2003 | Kieval et al. |
| 6,529,772 B2 | 3/2003 | Carlson et al. |
| 6,532,388 B1 | 3/2003 | Hill et al. |
| 6,542,774 B2 | 4/2003 | Hill et al. |
| 6,564,096 B2 | 5/2003 | Mest |
| 6,571,121 B2 | 5/2003 | Schroeppel et al. |
| 6,571,122 B2 | 5/2003 | Schroeppel et al. |
| 6,611,713 B2 | 8/2003 | Schauerte |
| 6,622,041 B2 | 9/2003 | Terry, Jr. et al. |
| 6,628,987 B1 | 9/2003 | Hill et al. |
| 6,628,988 B2 | 9/2003 | Kramer et al. |
| 6,647,289 B2 | 11/2003 | Prutchi |
| 6,678,547 B2 | 1/2004 | Carlson et al. |
| 6,690,971 B2 | 2/2004 | Schauerte et al. |
| 6,748,261 B1 | 6/2004 | Kroll et al. |
| 6,752,765 B1 * | 6/2004 | Strobel et al. ............... 600/536 |
| 6,763,267 B2 | 7/2004 | Ding |

| | | |
|---|---|---|
| 6,824,538 B2 | 11/2004 | Chen |
| 6,850,801 B2 | 2/2005 | Kieval et al. |
| 6,856,829 B2 | 2/2005 | Ohsaki et al. |
| 6,865,414 B1 | 3/2005 | Levine |
| 6,865,420 B1 | 3/2005 | Kroll |
| 6,915,160 B2 | 7/2005 | Auricchio et al. |
| 6,937,901 B2 | 8/2005 | Zhu et al. |
| 6,941,332 B2 | 9/2005 | Jensen |
| 6,965,797 B2 | 11/2005 | Pastore et al. |
| 6,973,349 B2 | 12/2005 | Salo |
| 7,062,314 B2 | 6/2006 | Zhu et al. |
| 7,065,405 B2 | 6/2006 | Pastore et al. |
| 7,069,070 B2 | 6/2006 | Carlson et al. |
| 7,079,888 B2 | 7/2006 | Oung et al. |
| 7,103,410 B2 | 9/2006 | Kramer et al. |
| 7,123,961 B1 | 10/2006 | Kroll et al. |
| 7,158,824 B2 | 1/2007 | Girouard et al. |
| 7,207,947 B2 * | 4/2007 | Koh et al. .................. 600/529 |
| 7,215,992 B2 | 5/2007 | Stahmann et al. |
| 7,260,431 B2 | 8/2007 | Libbus et al. |
| 7,277,761 B2 | 10/2007 | Shelchuk |
| 7,392,084 B2 | 6/2008 | KenKnight et al. |
| 2002/0058877 A1 | 5/2002 | Baumann et al. |
| 2002/0062139 A1 | 5/2002 | Ding |
| 2002/0107552 A1 | 8/2002 | Krig et al. |
| 2002/0107553 A1 | 8/2002 | Hill et al. |
| 2002/0120306 A1 | 8/2002 | Zhu et al. |
| 2002/0123768 A1 | 9/2002 | Gilkerson |
| 2002/0123769 A1 | 9/2002 | Panken et al. |
| 2002/0128563 A1 | 9/2002 | Carlson et al. |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2003/0004549 A1 | 1/2003 | Hill et al. |
| 2003/0303052 | 1/2003 | Hampton |
| 2003/0045909 A1 | 3/2003 | Gross et al. |
| 2003/0060848 A1 | 3/2003 | Kieval et al. |
| 2003/0060854 A1 | 3/2003 | Zhu |
| 2003/0060857 A1 | 3/2003 | Perrson et al. |
| 2003/0060858 A1 | 3/2003 | Kieval et al. |
| 2003/0069609 A1 | 4/2003 | Thompson |
| 2003/0078623 A1 | 4/2003 | Weinberg et al. |
| 2003/0078629 A1 | 4/2003 | Chen |
| 2003/0093002 A1 | 5/2003 | Kuo |
| 2003/0100924 A1 | 5/2003 | Foreman et al. |
| 2003/0105493 A1 | 6/2003 | Salo |
| 2003/0114889 A1 | 6/2003 | Huvelle et al. |
| 2003/0135126 A1 | 7/2003 | Kuo |
| 2003/0149450 A1 | 8/2003 | Mayberg |
| 2003/0191403 A1 * | 10/2003 | Zhou et al. .................. 600/515 |
| 2003/0199956 A1 | 10/2003 | Struble et al. |
| 2003/0212440 A1 | 11/2003 | Boveja |
| 2004/0019289 A1 | 1/2004 | Ross |
| 2004/0093034 A1 | 5/2004 | Girouard et al. |
| 2004/0093035 A1 | 5/2004 | Schwartz et al. |
| 2004/0102908 A1 | 5/2004 | Larson et al. |
| 2004/0116820 A1 | 6/2004 | Daum et al. |
| 2004/0133247 A1 | 7/2004 | Stahmann et al. |
| 2004/0158295 A1 | 8/2004 | Dyjach et al. |
| 2004/0215238 A1 | 10/2004 | van Dam et al. |
| 2004/0220636 A1 | 11/2004 | Burnes |
| 2004/0230241 A1 | 11/2004 | Carlson et al. |
| 2005/0065554 A1 | 3/2005 | KenKnight et al. |
| 2005/0149156 A1 | 7/2005 | Libbus et al. |
| 2005/0240237 A1 | 10/2005 | Zhu et al. |
| 2005/0261741 A1 | 11/2005 | Libbus et al. |
| 2006/0195038 A1 | 8/2006 | Carlson et al. |
| 2006/0206154 A1 | 9/2006 | Moffitt et al. |
| 2006/0241704 A1 | 10/2006 | Shuros et al. |
| 2006/0259088 A1 | 11/2006 | Pastore et al. |
| 2006/0287684 A1 | 12/2006 | Baynham et al. |
| 2008/0015648 A1 | 1/2008 | Libbus, I et al. |

FOREIGN PATENT DOCUMENTS

| | | |
|---|---|---|
| EP | 0709058 A1 | 1/1996 |
| EP | 0709112 | 5/1996 |
| EP | 1437159 A1 | 7/2004 |
| WO | WO-94/06350 | 3/1994 |
| WO | WO-98/15319 | 4/1998 |
| WO | WO-00/04950 | 2/2000 |
| WO | WO-00/38782 | 7/2000 |
| WO | WO-00/44274 A2 | 8/2000 |
| WO | WO-00/51680 | 9/2000 |
| WO | WO-02085448 A2 | 10/2002 |
| WO | WO-03020364 A2 | 3/2003 |
| WO | WO-2004012814 A1 | 2/2004 |
| WO | WO-2004033036 A2 | 4/2004 |
| WO | WO-2005113066 A1 | 10/2005 |
| WO | WO-2006079010 A1 | 7/2006 |
| WO | WO-2006121842 A3 | 11/2006 |

OTHER PUBLICATIONS

Behrens, S., et al., "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997),45-48.

Behrens, S., et al., "Modification of the Circadian Pattern of Ventricular Tachyarrhythmias by Beta-Blocker Therapy", *Clin. Cardiol.*, 20(3), (Mar. 1997),253-257.

Berger, R. D., et al., "An Efficient Algorithm for Spectral Analysis of Heart Rate Variability", *IEEE Transactions on Biomedical Engineering, BME-33 (9)*, (Sep. 1986),900-904.

Bigger, J. T., et al., "Correlations Among Time and Frequency Domain Measures of Heart Period Variability Two Weeks After Acute Myocardial Infarction", *Arrhythmias and Conduction Disturbances*, 69, (Apr. 1, 1992),891-898.

Bigger, Jr., J. T., "Spectral Analysis of R-R Variability to Evaluate Autonomic Physiology and Pharmacology and to Predict Cardiovascular Outcomes in Humans", *Am. J. Cardiol.*, 69(9), (Apr. 1, 1992),891-898.

Bilgutay, A M., et al., "Vagal tuning for the control of supraventricular arrhythmias", *Surgical Forum*, 16, (1965), 151-3.

Bilgutay, Aydin M., "Vagal tuning. A new concept in the treatment of supraventricular arrhythmias, angina pectoris, and heart failure", *Journal of Thoracic and Cardiovascular Surgery*, 56(1), (Jul. 1968). 71-82.

Böcker, D., et al., "Ventricular Resynchronization Therapy May Restore Autonomic Balance as Evidenced by Redicung the Low Frequency to High Frequency Autonomic Ratio in Heart Failure Patients", *4th International Meeting organized by the Working Group on Heart Failure of the European Society of Cardiology (Abstract)*, Barcelona, Spain,(Jun. 11, 2001). 1 p.

Borst, C , et al., "Optimal frequency of carotid sinus nerve stimulation in treatment of angina pectoris", *Cardiovascular Research*, 8(5), (Sep. 1974),674-80.

Braunwald, E., et al., "Carotid sinus nerve stimulation in the treatment of angina pectoris and supraventricular tachycardia", *California Medicine*, 112(3), (Mar. 1970),41-50.

Braunwald, E., et al., "Relief of angina pectoris by electrical stimulation of the carotid-sinus nerves", *New England Journal of Medicine*, 277(24), (Dec. 14, 1967),1278-83.

Cooper, T B., et al., "Neural effects on sinus rate and atrioventricular conduction produced by electrical stimulation from a transvenous electrode catheter in the canine right pulmonary artery", *Circulation Research*, 46(1), (Jan. 1980),48-57.

Courtice, G P., et al., "Effect of frequency and impulse pattern on the non-cholinergic cardiac response to vagal stimulation in the toad, Bufo marinus", *Journal of the Autonomic Nervous System*, 48(3), (Aug. 1994),267-72.

Crawford, Michael H., et al., "ACC/AHA Guidelines for Ambulatory Electrocardiography", *JACC*, vol. 34, No. 3, Published by Elsevier Science Inc.,(Sep. 1999),912-948.

Dart Jr., C H., et al., "Carotid sinus nerve stimulation treatment of angina refractory to other surgical procedures", *Annals of Thoracic Surgery*, 11(4), (Apr. 1971),348-59.

De Landsheere, D , et al., "Effect of spinal cord stimulation on regional myocardial perfusion assessed by positron emission tomography", *American Journal of Cardiology*, 69(14), (May 1, 1992),1143-9.

Epstein, S E. et al., "Treatment of angina pectoris by electrical stimulation of the carotid-sinus nerves", *New England Journal of Medicine*, 280(18), (May 1, 1969),971-8.

Farrehi, C , "Stimulation of the carotid sinus nerve in treatment of angina pectoris", *American Heart Journal*, 80(6), (Dec. 1970),759-65.

Feliciano, L , et al., "Vagal nerve stimulation releases vasoactive intestinal peptide which significantly increases coronary artery blood flow", *Cardiovascular Research*, 40(1), (Oct. 1998),45-55.

Fromer, M , et al., "Ultrarapid subthreshold stimulation for termination of atrioventricular node reentrant tachycardia", *Journal of the American College of Cardiology*, 20(4), (Oct. 1992), 879-83.

Hayano, J. et al., "Circadian Rhythms of Atrioventricular Conduction Properties in Chronic Artial Fibrillation With and Without Heart Failure", *JACC*, 31 (1), (Jan. 1998),pp. 158-166.

Henning, R J., "Effects of autonomic nerve stimulation, asynchrony, and load on $dP/dt_{max}$ and on $dP/dt_{min}$ ", *American Journal of Physiology*, 260(4 Pt 2), (Apr. 1991),H1290-8.

Henning, R J., et al., "Vagal nerve stimulation increases right ventricular contraction and relaxation and heart rate", *Cardiovascular Research, 32(5)*, (Nov. 1996),846-53.

Henning, R J., et al., "Vagal stimulation attenuates sympathetic enhancement of left ventricular function", *American Journal of Physiology*, 258(5 Pt 2), (May 1990),H1470-5.

Jessurun, G A., et al., "Coronary blood flow dynamics during transcutaneous electrical nerve stimulation for stable angina pectoris associated with severe narrowing of one major coronary artery", *American Journal of Cardiology*, 82(8), erratum appears in Am J Cardiol Feb. 15, 1999;83(4):642.(Oct. 15, 1998),921-6.

Lavery, C. E., et al., "Nonuniform Nighttime Distribution of Acute Cardiac Events", *Circulation*, 96(10), (Nov. 18, 1967),3321-3327.

Libbus, I. , et al., "Combined Remodeling Control Therapy and Anti-Remodeling Therapy by Implantable Cardiac Device", U.S. Appl. No. 10/850,341, filed May 20, 2004.

Mannheimer, C , et al., "Epidural spinal electrical stimulation in severe agina pectoris", *British Heart Journal*, 59(1), (Jan. 1988),56-51.

Mannheimer, C , et al., "Transcutaneous electrical nerve stimulation (TENS) in angina pectoris", *Pain*, 26(3), (Sep. 1986),291-300.

Mannheimer, C , et al., "Transcutaneous electrical nerve stimulation in severe angina pectoris", *European Heart Journal*, 3(4), (Aug. 1982),297-302.

Mazgalev, T N., et al., "Autonomic modification of the atrioventricular node during atrial fibrillation: role in the slowing of ventricular rate", *Circulation*, 99(21), (Jun. 1, 1999),2806-14.

Murphy, D F., et al., "Intractable angina pectoris: management with dorsal column stimulation", *Medical Journal of Australia*, 146(5), (Mar. 2, 1987),260.

No Authors Listed, "Heart rate variability: standards of measurement, physiological interpretation and clinical use. Task Force of the European Society of Cardiology and the North American Society of Pacing and Electrophysiology", *Circulation*, 93(5), (Mar. 1, 1996),1043-1065.

Peckova, M., et al., "Circadian Variations in the Occurence of Cardiac Arrests", *Circulation*, 98 (1), (1998),pp. 31-39.

Peters, T K., et al., "Temporal and spatial summation caused by aortic nerve stimulation in rabbits. Effects of stimulation frequencies and amplitudes", *Journal of the Autonomic Nervous System*, 27(3), (Aug. 1989). 193-205.

Peters, T K., et al., "The principle of electrical carotid sinus nerve stimulation: a nerve pacemaker system for angina pectoris and hypertension therapy", *Annals of Biomedical Engineering*, 8(4-6), (1980),445-58.

Schauerte, P , et al., "Catheter stimulation of cardiac parasympathetic nerves in humans: a novel approach to the cardiac autonomic nervous system", *Circulation*, 104(20), (Nov. 13, 2001),2430-5.

Schauerte, P N., et al., "Transvenous parasympathetic cardiac nerve stimulation: an approach for stable sinus rate control", *Journal of Cardiovascular Electrophysiology*, 10(11), (Nov. 1999),1517-24.

Schauerte, P , "Transvenous Parasympathetic Nerve Stimulation in the Inferior Vena Cava and Atrioventricular Conduction", *Journal of Cardiovascular Electrophysiology*, 11(1), (Jan. 2000),64-49.

Schauerte, P , et al., "Ventricular rate control during atrial fibrillation by cardiac parasympathetic nerve stimulation: a transvenous approach", *Journal of the American College of Cardiology*, 34(7), (Dec. 1999), 2043-50.

Scherlag, M A., "Endovascular Neural Stimulation Via a Novel Basket Electrode Catheter: Comparison of Electrode Configurations", *Journal of Interventional Cardiac Electrophysiology*, 4(1), (Apr. 2000),219-224.

Takahashi, N , "Vagal modulation of ventricular tachyarrhythmias induced by left ansae subclaviae stimulation in rabbits", *Japanese Heart Journal*, 39(4), (Jul. 1998),503-11.

Vanoli, E , "Vagal stimulation and prevention of sudden death in conscious dogs with a healed myocardial infarction", *Circulation Research*, 68(5), (May 1991),1471-81.

Wallick, D W., "Selective AV nodal vagal stimulation improves hemodynamics during acute atrial fibrillation in dogs", *American Journal of Physiology—Heart& Circulaltory Physiology*, 281(4), (Oct. 2001),H1490-7.

Waninger, M S., et al., "Electrophysiological control of ventricular rate during atrial fibrillation", *Pacing Clinical Electrophysiology*, 23(8), (Aug. 2000), 1239-44.

Yamashita, T., et al., "Circadian Variation of Paroxysmal Atrial Fibrillation", *Circulation*, 96(5), (Sep. 2, 1997),pp. 1537-1541.

Zhang, Y , et al., "Optimal ventricular rate slowing during atrial fibrillation by feedback AV nodal-selective vagal stimulation", *American Journal of Physiology—Heart & Circulatory Physiology*, 282(3), (Mar. 2002),H1102-10.

Zhou, X , et al., "Prevention of high incidence of neurally mediated ventricular arrhythmias by afferent nerve stimulation in dogs", *Circulation*, 101(7), (Feb. 22, 2000),819-24.

Carlson, Gerrard M., et al., "Statisical Method For Assessing Autonomic Balance", U.S. Appl. No. 11/382,568, Date mailed May 10, 2006, 21 pages.

Kochiadakis, G. F., "Autonomic nervous system activity before and during episodes of myocardial ischemia in patients with stable coronary artery disease during daily life", *Pacing Clin Electrophysiol.*, 23(12), (Dec., 2000),2030-9

Lanza, G. A., et al., "Usefulness of the Addition of Heart Rate Variability to Holter Monitoring in Predicting In-Hospital Cardiac Events in Patients With Unstable Angina Pectoris", *The American Journal of Cardiology*, 80(3), (Aug, 1, 1997),263-267.

Libbus, Imad , "Implantable Device for Treating Epilepsy and Cardiac Rhythm Disorders", U.S. Appl. No. 11/312,178, Filed Dec. 21, 2005, 39 Pages.

Vardas, P. E., et al., "Spectral analysis of heart rate variability before and during episodes of nocturnal ischaemia in patients with extensive coronary artery disease", *Eur Heart J.*, 17(3), (Mar., 1996),388-93.

"U.S. Appl. No. 10/436,876, Notice of allowance mailed Jan. 25, 2006", 15 pgs.

"U.S. Appl. No. 10/850,341, Non Final Office Action mailed May 31, 2006", 9 pgs.

"U.S. Appl. No. 10/850,341, Notice of Allowance mailed Apr. 5, 2007", 7 pgs.

"U.S. Appl. No. 10/850,341, Notice of Allowance mailed Nov. 30, 2006", 8 pgs.

"U.S. Appl. No. 10/850,341, Response filed Oct. 2, 2006 to Non Final Office Action mailed May 31, 2006", 10 pgs.

"Non-Final Office Action Mailed Aug. 28, 2007 in U.S. Appl. No. 10/728,124", 14 pgs.

"International Search Report for PCT Application No. PCT/US2004/031062", (Feb. 17, 2005), 5 pgs.

Koning, M M, "Rapid ventricular pacing produces myocardial protection by nonischemic activation of KATP+ channels", *Circulation*, 93(1), (Jan. 1, 1996), 178-186.

Murry, C. E., "Preconditioning with ischemia: a delay of lethal cell injury in ischemic myocardium", *Circulation*, 74(5), (1986), 1124-1136.

Scheiner, A., et al., "System and Method for Monitoring Autonomic Balance and Physical Activity", U.S. Appl. No. 10/695,430, filed Oct. 28, 2003, 20 pgs.

\* cited by examiner

SYSTEM AND METHOD FOR MONITORING AUTONOMIC BALANCE AND PHYSICAL ACTIVITY

TECHNICAL FIELD

This document relates generally to assessing cardio-neurological health and in particular, but not by way of limitation, to an implantable device for assessing health by monitoring autonomic balance while engaged in activities requiring various levels of exercise.

BACKGROUND

The autonomic nervous system includes a sympathetic component and a parasympathetic (or vagal) component. The sympathetic component is relatively slow acting and is associated with a tendency to raise heart rate, blood pressure, and cardiac output. The parasympathetic component provides a relatively fast response and is associated with a tendency to reduce heart rate, blood pressure, and cardiac output. A proper balance between the sympathetic and parasympathetic components is a characteristic of cardio-neurological health. Variously referred to as autonomic balance, autonomic tone, sympathetic tone or sympathovagal balance, such a metric provides an indication of the patient's well-being.

Autonomic tone is affected by physical activity. In a clinical setting, autonomic tone is measured while the patient engages in a prescribed activity. For example, autonomic tone will increase while a user transitions from a supine position to an upright position. A typical test of autonomic balance, called an orthostatic test, does not adequately provide information as to tone over an extended period of time.

SUMMARY

One embodiment of the present subject matter provides an implantable cardiac rhythm management device adapted to continuously monitor autonomic tone and physical activity. Patient specific baseline data for a predetermined time, or epoch, is generated and reported. In one embodiment, therapy is tailored according to the current relationship between autonomic tone and activity level and a baseline level.

In one embodiment, the baseline data includes data corresponding to a selected population or data corresponding to historical performance of the patient.

The present subject matter allows tracking of different levels of stress (as measured by activity) while monitoring autonomic tone. Physiological conditions can be identified by abnormalities in the relationship between autonomic tone and level of activity. In one embodiment, the activity level and autonomic tone are presented over a period of time as a footprint.

One embodiment provides sensors tailored to monitor autonomic tone and physical activity level wherein at least one sensor is implanted. Data from the two sensors is correlated by a processor. The processor, in various embodiments, is implanted or externally located. The autonomic tone and physical activity data is available for managing therapy or further analysis.

Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present subject matter. The following detailed description is, therefore, not to be taken in a limiting sense, and the scope of the present invention is defined by the appended claims and their equivalents.

Figure 1:
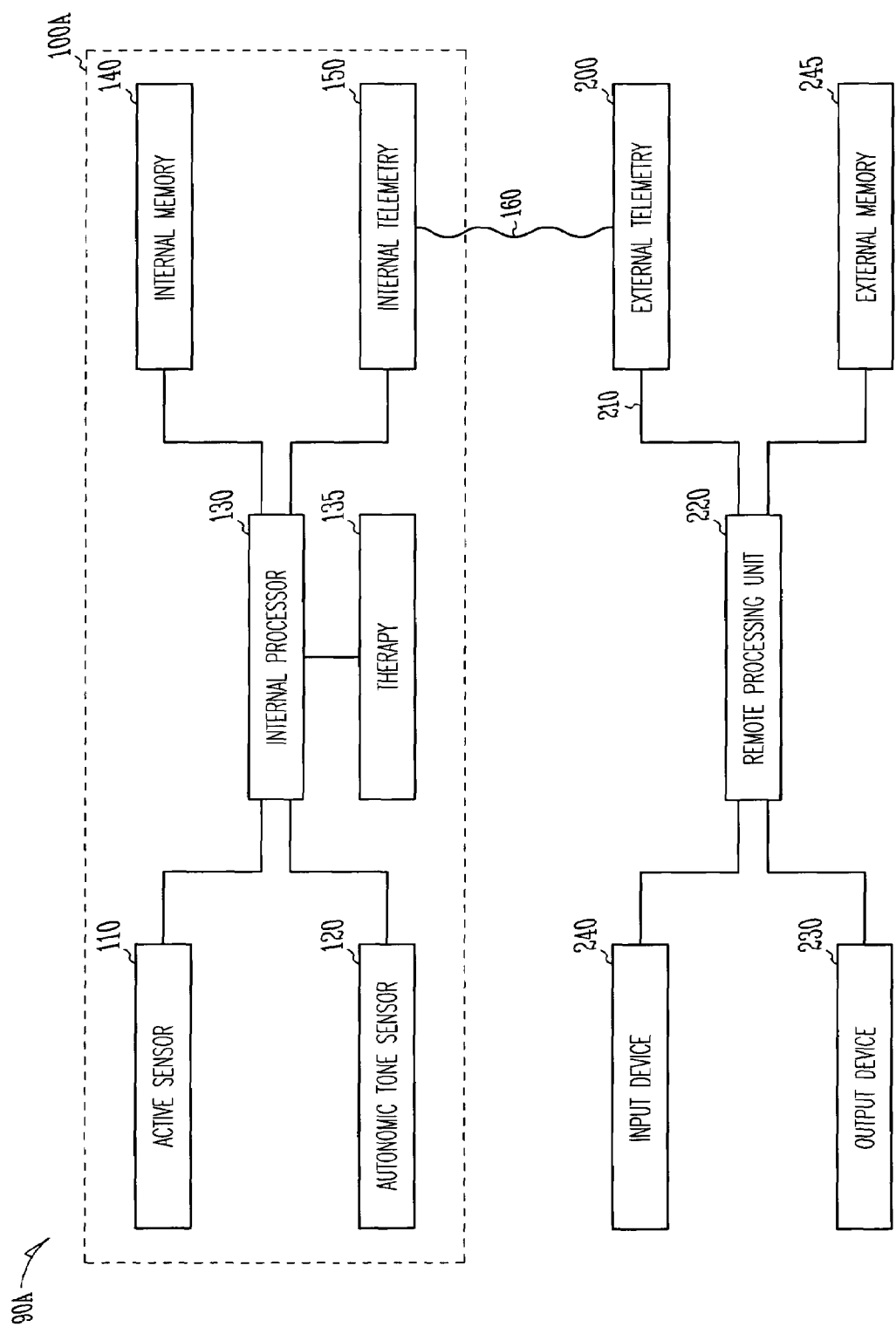
FIG. 1 illustrates a block diagram of a cardiac rhythm management system according to one embodiment of the present subject matter.

FIG. 1 illustrates a block diagram of system 90A according to one embodiment of the present subject matter. System 90A includes implantable unit 100A and external components. In the figure, implantable unit 100A includes activity sensor 110, autonomic tone sensor 120, internal processor 130, therapy unit 135, internal memory 140 and internal telemetry unit 150. External components include external telemetry unit 200, remote processing unit 220, input device 240 and output device 230 and external memory 245.

Implantable unit 100A includes an implantable housing as well as leads and electrodes adapted to couple with one or more selected organ. In one embodiment, for example, activity sensor 110 includes a minute ventilation sensor and autonomic tone sensor 120 includes a heart rate sensor that provides a signal based on heart rate variability.

In various embodiments, activity sensor 110 includes an adaptive rate therapy sensor, examples of which include a minute ventilation sensor, an accelerometer, a respiratory sensor, a QT interval sensor, an impedance sensor, a contractility sensor and a depolarization sensor.

In various embodiments, autonomic tone sensor 120 includes a sensor to provide a signal based on the sympathetic nervous system and the parasympathetic nervous system. Autonomic tone sensor 120, in various embodiments, includes a heart rate variability sensor, a nerve electrode, a biochemical sensor and a muscle activity sensor. In one embodiment, autonomic tone sensor 120 includes a chemical sensor to monitor a drug level, such as norepinephrine, or a hormone level, such as B-type natriuretic peptide (BNP). B-type natriuretic peptide is a blood borne cardiac hormone that responds to ventricular wall stretch and blood pressure and is associated with symptoms of heart failure.

Internal processor 130 includes, in one embodiment, an information processing unit. Internal processor 130 receives an activity signal from activity sensor 110 and a tone signal from autonomic tone sensor 120 and stores a code, or data, in internal memory 140 correlating autonomic tone and physical activity. In one embodiment, internal processor 130 provides an output signal based on the relationship between autonomic tone and physical activity level. Internal processor 130, in various embodiments, includes a digital processor, such as a microprocessor, or an analog processor. In one embodiment, internal processor 130 executes programming to control the operation of therapy unit 135.

Therapy unit 135, also coupled to internal processor 130, includes circuitry and hardware to deliver therapy based on the autonomic tone and physical activity. In one embodiment, therapy unit 135 includes a pulse generator and provides pacing pulses. In one embodiment, therapy unit 135 includes a drug delivery device.

Internal telemetry unit 150, also coupled to internal processor 130, includes a wireless transceiver for communicating with external telemetry unit 200, as shown by communication link 160. In one embodiment, communication link 160 is bidirectional and in another embodiment, communication link 160 is unidirectional.

External telemetry unit 200 is coupled to remote processing unit 220 by link 210. Remote processing unit 220 is also connected to input device 240, output device 230 and external memory 245. In one embodiment, external telemetry unit 200, link 210, remote processing unit 220, input device 240, output device 230 and external memory 245 are housed in a single unit sometimes referred to as a programmer. In one embodiment, the external components are distributed. For example, in one embodiment, link 210 includes a digital communication network. Examples of digital communication networks include a local area network or a wide area network such as the Internet.

Remote processing unit 220, in various embodiments, includes a digital processor, such as a microprocessor, or an analog processor.

Input device 240 includes a keyboard, mouse, card reader or other user operable data communication device. Output device 230 includes a display monitor, audio speaker, printer or other device to provide data to an operator. External memory 245, in various embodiments, includes random access memory (RAM), read only memory (ROM), optical storage medium, magnetic storage medium or other stationary or removable memory medium.

Figure 2:
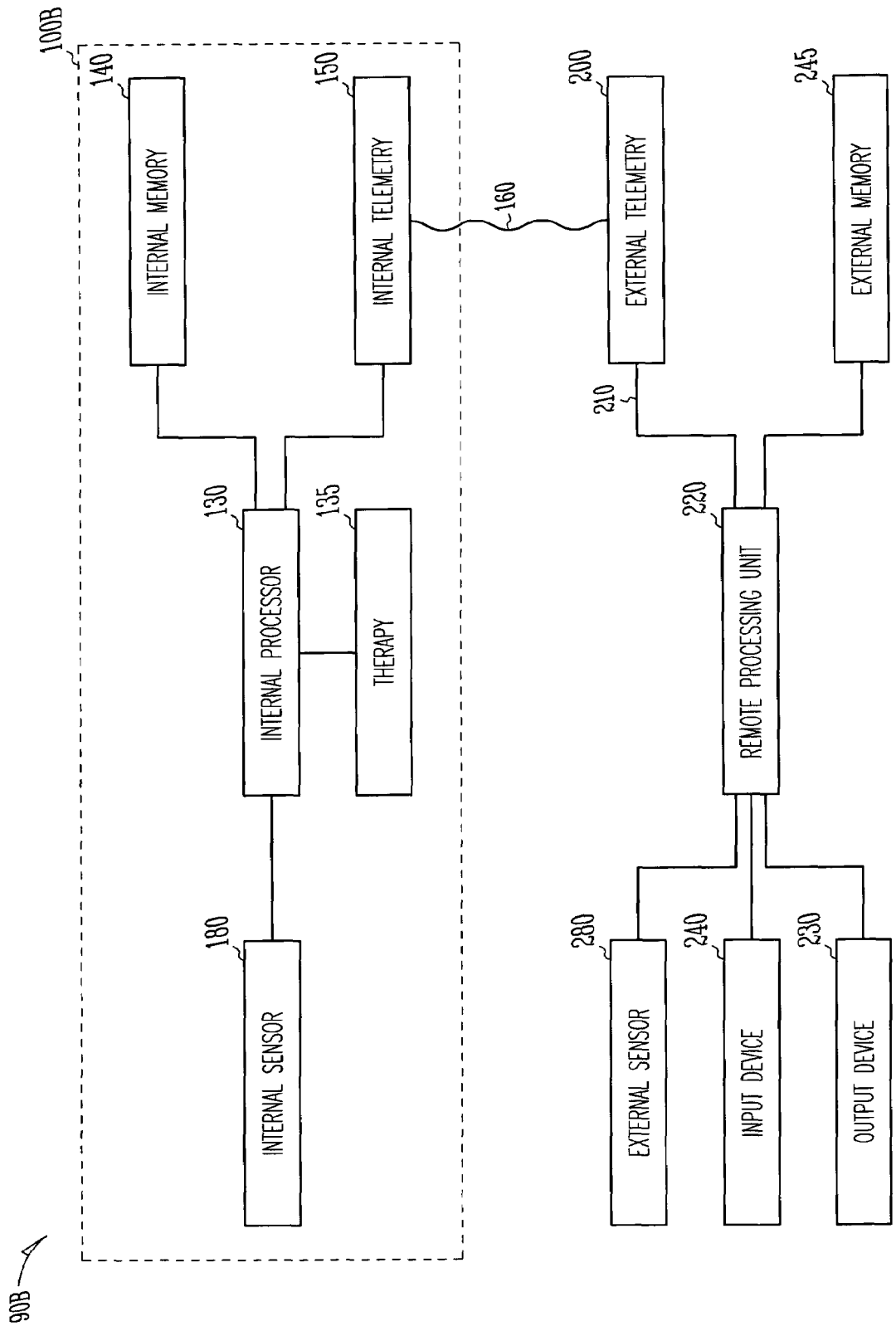
FIG. 2 illustrates a block diagram of a cardiac rhythm management system according to one embodiment of the present subject matter.

FIG. 2 illustrates a block diagram of system 90B according to one embodiment of the present subject matter. System 90B includes implantable unit 100B and external components. In the figure, implantable unit 100B includes internal sensor 180, internal processor 130, therapy unit 135, internal memory 140 and internal telemetry unit 150. External components include external telemetry unit 200, remote processing unit 220, input device 240, output device 230, external memory 245 and external sensor 280.

Internal sensor 180, in one embodiment, includes an autonomic tone sensor and external sensor 280 includes an activity sensor, each of which are described elsewhere in this document. For example, in one embodiment, internal sensor 180 includes a heart rate variability sensor and external sensor 280 includes an activity monitor coupled to an exercise machine such as a stationary treadmill. External sensor 280, in various embodiments, is part of an apparatus used for exercising or part of diagnostic equipment in a clinical setting or a health care facility.

Internal sensor 180, in one embodiment, includes an activity sensor and external sensor 280 includes an autonomic tone sensor. For example, in one embodiment, internal sensor 180 includes an accelerometer responsive to physical activity and external sensor 280 includes a heart rate monitor responsive to heart rate variability.

Remote processing unit 220 receives an activity signal and an autonomic tone signal from the combination of internal sensor 180 and external sensor 280 and stores data in external memory 245 accessible to remote processing unit 220. The stored data correlates the autonomic tone and physical activity. Output device 230 is coupled to remote processing unit 220 and provides a visible or audible representation of autonomic tone and physical activity.

In one embodiment, remote processing unit 220 executes programming to determine therapy, validate therapy or manage therapy as a function of the autonomic tone and physical activity. For example, following a determination calling for a more rapid pacing rate, a signal from remote processing unit 220 is communicated via link 210 and external telemetry unit 200 to internal telemetry unit 150 for delivery to internal processor 130. Internal processor 130 then instructs therapy unit 135 to increase the pacing rate.

Figure 3:
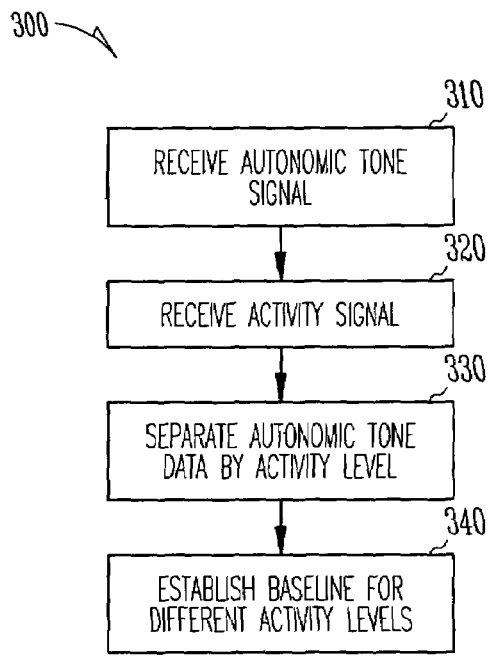
FIG. 3 illustrates a method according to one embodiment of the present subject matter.

FIG. 3 illustrates method 300 according to one embodiment of the present subject matter. In the figure, a performance baseline for a patient is established. At 310, an autonomic tone signal is received from an autonomic tone sensor. In various embodiments, the sensor is implantable or externally located. At 320, an activity signal is received from an activity sensor. The activity sensor, in various embodiments, is implantable or externally located.

At 330, a program executing on a processor operates to separate the autonomic tone data by an activity level as indicated by the activity signal. At 340, a baseline is established to correlate different activity levels with an autonomic tone. The baseline, in one embodiment, is a compilation of data for a particular user. In one embodiment, the baseline is an aggregate of the data for a particular user and a selected population. The population may be selected on the basis of medical conditions, geographical location or other factors. In one embodiment, the baseline is an evolving metric that begins with seed information derived from a selected population and is tailored with data derived from a particular user. Over a period of time, the population data is attenuated and the comparison data becomes predominantly that of the patient. For example, in one embodiment, the baseline data includes a population norm value for a class IV heart failure event. Other methods to incorporate a population norm as part of a baseline are also contemplated.

Consider an exemplary embodiment utilizing an accelerometer for the physical activity component of the baseline. The accelerometer provides an output measured in units of gravity "G" or milli-G. In one embodiment, autonomic tone is measured while the user is engaged in physical activities, including when at a predetermined state of rest, when at a predetermined level of exercise, when transitioning from the predetermined state of rest to the predetermined level of exercise and when recovering, or transitioning, from the predetermined level of exercise to the predetermined state of rest. For each of these conditions, a measure of autonomic tone is generated. In one embodiment, the baseline reflects the patient norms for each of these different conditions. In one embodiment, the baseline reflects a population norm for each of these different conditions.

In one embodiment, the baseline for a normal patient can be described, in the frequency spectrum, as transitioning from a supine position to a vertical position.

In one embodiment, the baseline is quantized to allow identification and analysis of departures from normal performance. For example, an improving condition may be denoted as a reduced differential between the baseline and a measured condition of autonomic tone and activity level.

Using an accelerometer, an activity level can be described by comparing measured accelerations with predetermined acceleration thresholds while engaged in that activity or condition for a predetermined period of time. For example, the user can be described as "at rest" when an acceleration level remains below a particular minimum level for a minimum time period. Discrete acceleration levels may be derived from an average measured acceleration for a window having a predetermined width in time. Filters and other functions may be applied to the acceleration levels to quantify a measured parameter.

In one embodiment, the activity level is determined based on a measurement of an autonomic tone. For example, when autonomic tone is measured at a predetermined level, data corresponding to a measured activity level is stored in a memory. Other methods of separating autonomic tone by activity level are also contemplated.

In one embodiment, analysis of a trend in data is performed. Trend analysis includes evaluating changes in the patient's baseline over a period of time. Trends can be evaluated based on comparisons with data from the patient or from a selected population.

In one embodiment, a range of activity levels is established for a particular patient. For example, the functional capacity range, which describes the difference between a rest activity level and a highest exertion activity level, is separated into predetermined divisions. In one embodiment, the functional capacity range is quartiled. The range then provides a means for classifying autonomic tone by activity level.

In one embodiment, multiple baselines are established for a particular patient. For example, in one embodiment, a resting baseline and a maximum exertion baseline is created at the time of implantation of the present subject matter. After a predetermined period of time, the resting baseline and maximum exertion baseline data are compared with current measurements.

In one embodiment, when the relationship between autonomic tone and exertion level (or activity level) indicates an unhealthy or dangerous condition, a warning signal is generated. The warning signal can be provided to the patient, physician or to a monitoring facility. The warning signal provided to a patient may be, for example but not limited to, in the form of a tactile message or audible message and delivered by means of a suitable transducer. The level at which a warning signal is generated, in one embodiment, is selectable by, for example, programming. The warning signal may be tailored to provide notice upon detecting a severely out of balance condition.

In one embodiment, a comparison is made between a norm for a selected population and that of a particular patient's autonomic tone and exertion level. Normative values permit classifying the health of the patient.

Figure 4:
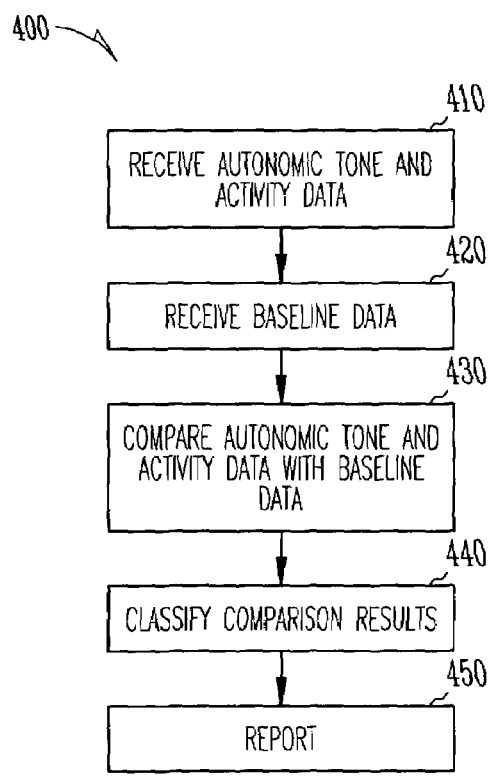
FIG. 4 illustrates a method according to one embodiment of the present subject matter.

FIG. 4 illustrates method 400 according to one embodiment. At 410, autonomic tone data and activity data is received. In addition, baseline information is received at 420. At 430, the received autonomic tone data and activity data is compared with the received baseline data. As a function of the comparison, the autonomic tone and activity data is classified, at 440. For baseline data reflective of a selected population, the classification yields a ranking of the user compared to that population. For baseline data reflective of a particular user, the classification will yield comparative health of the user as compared to that user's general health. At 450, the classification information is reported. Reporting, in one embodiment, includes transdermal communication of the data to a remote programmer.

Alternative Embodiments

A measure of autonomic tone can be derived from heart rate variability. In one embodiment, heart beats are represented by an R-R chart where the horizontal axis corresponds to beats and the vertical axis to time. A spectral analysis of the R-R data reveals content in different frequency bands, including very low frequency components (typically below 0.04 Hz), low frequency components (typically 0.04-0.15 Hz) and high frequency components (typically 0.15-0.4 Hz). A correlation exists between the power spectral density of high frequency band content and the tone of the parasympathetic nervous system and between the power spectral density of low frequency band content and the tone of the sympathetic nervous system. Thus, autonomic tone, according to one embodiment, is a ratio of low frequency signal power to high frequency signal power.

In one embodiment, either or both of the activity sensor and autonomic tone sensor includes a sensor configured to chronically or invasively provide data. In one embodiment, the sensor is included in a housing adapted for implantation. In one embodiment, the sensor is coupled by an electrode to a remote housing that is also implanted.

In one embodiment, the present subject matter evaluates one or more sensors corresponding to autonomic tone or physical activity. For example, in one embodiment, autonomic tone data is derived from both a heart rate sensor providing a signal corresponding to heart rate variability and a drug level sensor providing a signal corresponding to BNP. As another example, in one embodiment, physical activity data is derived from both a stationary treadmill (or other exercise machine) and an accelerometer. In various embodiments, more than one sensor is used to provide autonomic tone data or physical activity data.

In one embodiment, a graphical tool is used to depict autonomic tone data and physical activity data over a period of time. One such tool is an adaptation of a particular histogram sometimes referred to as a footprint. Commonly assigned U.S. Pat. Nos. 6,026,320, 5,603,331, 6,301,499 and 6,529,772 describe footprints and are each incorporated herein by reference. The footprint provides an aggregate picture of autonomic tone (as measured, for example by R-R interval) over a period of time.

The footprint, in one embodiment, includes a histogram having a vertical axis corresponding to the absolute value of the difference between adjacent R-R intervals and the horizontal axis corresponding to R-R interval in milliseconds. In one embodiment, the histogram is calibrated in terms of a heart rate with horizontal axis dimensions in milliseconds. The image is a histogram of the occurrence of coded values with each value denoted by the height of the histogram at those locations. During a 24 hour period, for example, all sinus beats are captured and the lowest heart rate achieved appears on the left hand side and the highest rate achieved appears on the right. The difference between the highest and lowest rate corresponds to breadth of heart rate reserve. Increased heart rate variability is indicated by an increased height of the footprint. Greater cardiac reserve is indicated on the footprint by greater width. A mean heart rate is sometimes shown on the footprint with a vertical line.

Other periods of time for the footprint are also contemplated. For example, in one embodiment, weekly, monthly or annual average footprint data is compiled.

The footprint is adapted to illustrate physical activity data corresponding to the autonomic tone data. Various methods can be used to depict the physical activity level and autonomic tone data. In one method, physical activity data is mapped to a predetermined variable. The footprint images are created continuously and thus, at each activity level, a new image is created. This method provides a histogram having three dimensions where the third dimension represents an activity level. For example, over a 24 hour period, one embodiment of the present subject matter yields a footprint having a melon-shaped region with different slices through the region corresponding to different physical activity levels for the period. In one embodiment, a slice through the left most edge of the region, corresponds to autonomic tones at a low activity level occurring throughout the 24 hour period and a slice through the right most edge of the region corresponds to autonomic tones at a high activity level occurring throughout the 24 hour period.

In one method, the footprint is presented as a color coded histogram overlaid atop a grey scale where different colors correspond to different physical activity levels.

In one embodiment, an instantaneous physical activity level is compared with autonomic tone. In one embodiment, a processor controlled algorithm is used to determine an activity level. For example, in one embodiment, a time frame is established and a physical activity level is recognized when a sensor reading has stabilized to within a predetermined range of values. In one embodiment, a stable acceleration level, expressed in milli-G's over a predetermined time period of 30 seconds is associated with a recognized activity level. For each recognized activity level, an autonomic tone metric is also recorded. In one embodiment, an average or minimum duration is taken as a valid reading of physical activity.

Other filtering means are also contemplated for capturing valid data and suppressing spurious readings. For example, a minimum acceleration sensor signal level can be established for a minimum duration. In various embodiments, different windows of time are prescribed wherein, for example, a minimum activity for a period of one second, 30 seconds or one minute window is a recognized duration. For example, in one embodiment, an acceleration in the range of 10 to 20 milli-Gs lasting for a duration between 2 and 3 minutes is deemed to be a valid activity level. Other bands of acceleration magnitudes and duration are also contemplated.

In one embodiment, a predetermined signal received from a first activity sensor is used to recognize a minimum activity level and a second activity sensor is then correlated with a measured autonomic tone.

In one embodiment, a combination of multiple activity sensors are mapped to an activity index. The activity index is correlated with an autonomic tone measurement.

In various embodiments, the stored data is available for managing therapy and later analysis. The stored data is available for further analysis by a remotely located processor. In one embodiment, a monitor provides storage for the autonomic tone and physical activity data.

In one embodiment, a physical activity sensor is coupled to an exercise machine and an autonomic tone sensor is implanted in a patient. The autonomic tone sensor data is communicated to an external device by a telemetry circuit. A remote processor, coupled by a network connection receives both the physical activity sensor data and the autonomic tone sensor data. The remote processor executes programming to diagnose the received data. In one embodiment, therapy instructions are transmitted from the remote processor, via the network, to an implanted therapy circuit. In one embodiment, an implanted processor receives the data from the physical sensor and performs diagnostic functions, manages therapy and stores data. In various embodiments, the exercise machine includes a treadmill, bicycle, climbing machine, weight lifting or weight moving machine, rowing machine or other exercise equipment. In various embodiments, the signal generated by the exercise machine may correlate to a measure of power, calories, speed, oxygen uptake or other measure of physical activity. The exercise machine may be stationary or mobile.

Other combinations are also contemplated. For example, in one embodiment, the physical activity level is measured by an implanted device and an external sensor is used to provide autonomic tone data. As another example, in one embodiment, both the physical activity level and the autonomic tone are measured by an implantable sensor.

In one embodiment, each activity level is correlated with autonomic tone. In one embodiment, autonomic tone is correlated with each activity level.

CONCLUSION

The above description is intended to be illustrative, and not restrictive. Many other embodiments will be apparent to those of skill in the art upon reviewing the above description.

What is claimed is:

1. An implantable device comprising:
    an autonomic tone sensor to provide a tone signal as a function of a sympathetic nervous system and as a function of a parasympathetic nervous system for a predetermined period of time;
    an activity sensor to provide an activity signal as a function of physical activity corresponding to the predetermined period; and
    an information processing unit connected to the autonomic tone sensor and connected to the activity sensor and adapted to generate an output signal based upon a relationship between the tone signal and the activity signal, establish a baseline that correlates different tone signals with different activity signals over a predetermined period of time, compare the output signal to the baseline, and classify a patient's health status based upon the comparison.

2. The device of claim 1 wherein the autonomic tone sensor includes at least one sensor selected from any combination of a group including a heart rate sensor, a nerve electrode, a biochemical sensor, a ventilation sensor and a muscle activity sensor.

3. The device of claim 1 wherein the activity sensor includes an adaptive rate therapy sensor.

4. The device of claim 1 wherein the activity sensor includes at least one sensor selected from any combination of a group including a minute ventilation sensor, an accelerometer, a respiratory sensor, a QT interval sensor, an impedance sensor, a contractility sensor and a depolarization sensor.

5. The device of claim 1 further including a telemetry circuit connected to the information processing unit to communicate with a remote device.

6. The device of claim 1 further including a therapy circuit connected to the information processing unit.

7. The device of claim 6 wherein the therapy circuit includes a pulse generator.

8. The device of claim 1 further including a memory connected to the information processing unit and adapted to store a code as a function of the output signal.

9. The device of claim 1 wherein the autonomic tone sensor includes an implanted electrical lead.

10. The device of claim 1 wherein the information processing unit includes a processor.

11. A method comprising:
generating an autonomic tone signal as a function of autonomic tone detected during an epoch using an implantable sensor;
obtaining an activity signal as a function of physical activity during the epoch; and
generating an output signal based upon a relationship between the tone signal and the activity signal, establishing a baseline that correlates different tone signals with different activity signals over a predetermined period of time, comparing the output signal to the baseline, and classifying a patient's health status based upon the comparison.

12. The method of claim 11 wherein generating an autonomic tone signal includes determining heart rate variability.

13. The method of claim 12 wherein determining heart rate variability includes measuring intervals between successive heart beats.

14. The method of claim 11 wherein obtaining the activity signal includes receiving a minute ventilation signal.

15. The method of claim 14 wherein receiving the minute ventilation signal includes determining an impedance.

16. The method of claim 11 wherein obtaining the activity signal includes receiving an acceleration signal.

17. The method of claim 11 further including classifying the autonomic tone signal as a function of the activity signal for the epoch.

18. The method of claim 17 further including comparing the epoch with stored data accessible to an implantable processor.

19. The method of claim 18 wherein the stored data includes data derived from a selected population.

20. The method of claim 11 wherein generating an output signal includes providing a warning.

* * * * *

UNITED STATES PATENT AND TRADEMARK OFFICE
CERTIFICATE OF CORRECTION

PATENT NO. : 7,572,226 B2 Page 1 of 1
APPLICATION NO. : 10/695430
DATED : August 11, 2009
INVENTOR(S) : Scheiner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1210 days.

Signed and Sealed this

Seventh Day of September, 2010

David J. Kappos
*Director of the United States Patent and Trademark Office*